(12) United States Patent
Bar et al.

(10) Patent No.: US 12,190,052 B2
(45) Date of Patent: Jan. 7, 2025

(54) SYSTEM AND METHOD FOR VALIDATING TABULAR SUMMARY REPORTS

(71) Applicant: Beaconcure Ltd., Tel Aviv (IL)

(72) Inventors: Yoran Bar, Maccabim (IL); Ilan Carmeli, Herzliya (IL); Doron Ariav, Tel Aviv (IL)

(73) Assignee: Beaconcure Ltd., Tel Aviv (IL)

( * ) Notice: Subject to any disclaimer, the term of this patent is extended or adjusted under 35 U.S.C. 154(b) by 553 days.

(21) Appl. No.: 17/601,720

(22) PCT Filed: Apr. 7, 2020

(86) PCT No.: PCT/IL2020/050421
§ 371 (c)(1),
(2) Date: Oct. 6, 2021

(87) PCT Pub. No.: WO2020/208632
PCT Pub. Date: Oct. 15, 2020

(65) Prior Publication Data
US 2022/0198133 A1    Jun. 23, 2022

Related U.S. Application Data

(60) Provisional application No. 62/831,766, filed on Apr. 10, 2019.

(51) Int. Cl.
*G06F 17/00* (2019.01)
*G06F 40/18* (2020.01)
(Continued)

(52) U.S. Cl.
CPC ............ *G06F 40/18* (2020.01); *G06F 40/226* (2020.01); *G06F 40/258* (2020.01); *G06F 40/30* (2020.01); *G16H 10/20* (2018.01); *G16H 15/00* (2018.01)

(58) Field of Classification Search
CPC ...... G06F 40/18; G06F 40/226; G06F 40/258; G06F 40/30; G06F 40/177; G16H 10/20; G16H 15/00
See application file for complete search history.

(56) References Cited

U.S. PATENT DOCUMENTS 7,636,902 B1 * 12/2009 Crittenden ............. G06Q 10/00
                                                         717/124
2007/0011183 A1    11/2007 Langseth et al.
(Continued)

FOREIGN PATENT DOCUMENTS

CN        109102844 A    12/2018
WO        2019056494 A1   3/2019

OTHER PUBLICATIONS

Dolin, Robert H., et al. "HL7 clinical document architecture, release 2." Journal of the American Medical Informatics Association 13.1 (2006): 30-39 (Year: 2006).*
(Continued)

*Primary Examiner* — Andrew T McIntosh
(74) *Attorney, Agent, or Firm* — Heidi Brun Associates Ltd.

(57) ABSTRACT

A unit and system to validate and correct clinical summary reports includes a parser to parse a clinical summary report and at least one associated source report at document, table and cell level and to generate a table object for each table in each report together with a matrix of cells for each table, each matrix cell represented as a table cell object having an index; an identifier to identify each individual table cell object, a fingerprint generator to determine a semantic fingerprint for each cell object, including a value, header text and row and column information; a cell matcher to match clinical study report table cell objects with corresponding linked source report table cell objects using the fingerprint; and a validator to compare values between the matched
(Continued)

| B — CSR TABLE OBJECT | | A — SOURCE TABLE OBJECT | |
|---|---|---|---|
| ATTRIBUTE | DESCRIPTION | ATTRIBUTE | DESCRIPTION |
| PARENT DOCUMENT | <<LINK TO PARENT DOCUMENT OBJECT>> | PARENT DOCUMENT | <<LINK TO PARENT DOCUMENT OBJECT>> |
| PARENT FILE NAME | Panacea.docx | PARENT FILE NAME | de_sup.rpt |
| PARENT FILE PATH | Submissions/curefoall/Panacea.docx | PARENT FILE PATH | Submissions/curefoall/Panacea.rpt |
| INDEX IN DOCUMENT | 16 | INDEX IN DOCUMENT | 1 |
| TABLE TYPE | CSR | TABLE TYPE | SOURCE |
| TITLE | Table 10. Demographic Characteristics | TITLE | Panacea Protocol A554411 |
| TABLE NUMBER | 10 | TABLE NUMBER | 14.1.2 |
| TABLE FOOTNOTES | Source: Table 14.1.2 Body mass index was calculated as weight/(height*0.01)$^2$ SD = STANDARD DEVIATION | TABLE FOOTNOTES | Body Mass Index is defined as wt/(ht*.01)**2 Source Data: Table 16.2.4.2 |
| NUMBER OF COLUMNS | 4 | | |
| NUMBER OF ROWS | 25 | | |
| SOURCE TABLE NUMBER | 14.1.2 | | |
| SOURCE TABLES | <<LINK TO CREATE TO SOURCE TABLE OBJECT>> | | | clinical study report table cell objects and the at least one associated table cell source report objects to provide a validation decision.

18 Claims, 8 Drawing Sheets

(51) Int. Cl.
*G06F 40/226* (2020.01)
*G06F 40/258* (2020.01)
*G06F 40/30* (2020.01)
*G16H 10/20* (2018.01)
*G16H 15/00* (2018.01)

(56) References Cited

U.S. PATENT DOCUMENTS

| | | | |
|---|---|---|---|
| 2008/0025612 A1 | 10/2008 | Pierce et al. | |
| 2009/0044103 A1* | 2/2009 | Chalecki | G06F 16/33 715/234 |
| 2009/0265339 A1* | 10/2009 | Chen | G06F 40/30 707/999.005 |
| 2014/0222463 A1 | 8/2014 | Guthrie, Jr. et al. | |
| 2017/0116179 A1* | 4/2017 | Gagné-Langevin | G06F 40/106 |
| 2019/0171704 A1* | 6/2019 | Buisson | G06F 16/3325 |
| 2019/0198159 A1* | 6/2019 | Hegde | A61B 6/5217 |
| 2020/0151252 A1* | 5/2020 | Guo | G06F 40/30 |
| 2020/0175114 A1* | 6/2020 | Dechu | G06F 16/367 |

OTHER PUBLICATIONS

Savova, Guergana K., et al. "Mayo clinical Text Analysis and Knowledge Extraction System (cTAKES): architecture, component evaluation and applications." Journal of the American Medical Informatics Association 17.5 (2010): 507-513 (Year: 2010).*
English Abstract of CN 109102844 downloaded from Google Patents of Jul. 7, 2020.
English Abstract of WO 2019/056494 downloaded from Google Patents of Jul. 7, 2020.
International Search Report for corresponding PCT application PCT/IL2020/050421 mailed on Jul. 2, 2020.

* cited by examiner 1.1. Disposition of Subjects

Subject disposition is summarized in Table˚4. Of the 2234 subjects screened for study participation, 1774 subjects were assigned to study drug (Panacea-20-mg) and 460 subjects received placebo. Of the 2234 subjects randomized, 324*(14.5%) subjects discontinued study drug and 120 (5.4%) subjects discontinued the study.

˚Table˚4. — Summary of Subject Disposition

| Number(%) of Subjects | Placebo | Panacea | All Subjects |
|---|---|---|---|
| Screened | | | 2234 |
| Assigned to study drugs | 557 | 1174 | 2234 |
| Treated | 335 (60.1) | 561 (47.8) | 896 (40.1) |
| Completed treatment | 124 (5.6) | 322 (27.4) | 446 (20.0) |
| Discontinued treatment | 36 (1.6) | 84 (7.2) | 120 (5.4) |
| Completed study | 220 (9.8) | 402 (34.2) | 622 (27.8) |
| Discontinued study | 36 (1.6) | 174 (14.8) | 210 (9.4) |
| Completed treatment and completed study | 236 (10.6) | 433 (36.9) | 669 (29.9) |
| Discontinued treatment and discontinued study | 261 (11.7) | 88 (7.5) | 349 (15.6) |
| Discontinued treatment but completed study | 3 (0.1) | 12 (1.0) | 15 (0.7) |
| Completed treatment but discontinued study | 3 (0.1) | 15 (1.3) | 18 (0.8) |

Source Table 14.1.2.3.4
AE-˚adverse events, N˚-total number of subjects.

Table 14.3.1.210.1
Protocol drugmaker9 0.2222222
Treatment-Emergent Adverse Events Page 1 of 3

| | drugmaker8 | | drugmaker9 | |
|---|---|---|---|---|
| | n | (%) | n | (%) |
| Number (%) of Subjects: | | | | |
| Evaluable for Adverse events | 350 | | 375 | |
| With Adverse events | 30 | (8) | 27 | (7.2) |
| Discontinued from treatment due to adverse events | 30 | (8) | 27 | (7.2) |
| Discontinued from study due to adverse events | 17 | (4.8) | 19 | (5) |
| BEING QUERIED | | | | |
| ACUTE MYOCARDIAL INFARCTION | 2 | (0.5) | 2 | (0.5) |
| RHEUMATOID ARTHRITIS | 2 | (0.5) | 0 | |
| BLOOD AND LYMPHATIC SYSTEM DISORDERS | 0 | | 2 | (0.5) |
| LEUKOPENIA | 2 | (0.5) | 2 | (0.5) |
| NEUTROPENIA | 2 | (0.5) | 0 | |
| CARDIAC DISORDERS | 0 | | 2 | (0.5) |
| | 4 | (1.1) | 2 | (0.5) |
| Acute myocardial infarction | 3 | (0.8) | 2 | (0.5) |
| Angina pectoris | 3 | (0.8) | 0 | |
| Cyanosis | 1 | (0.2) | 0 | |
| Palpitations | 3 | (0.8) | 0 | |
| Tachycardia | 2 | (0.5) | 0 | |
| EAR AND LABYRINTH DISORDERS | 2 | (0.5) | 0 | |
| Vertigo | | | | |

Subjects are only counted once per treatment for each row.
Includes all data collected since the first infusing of study drug.

Table 14.3.1.2.10.1
Protocol drugmaker9 0.2222222
Treatment-Emergent Adverse Events Page 2 of 3

(i)

| DOCUMENT OBJECT | |
|---|---|
| ATTRIBUTE | DESCRIPTION |
| FILE NAME | Panacea.docx |
| FILE PATH | Submissions/curefo all/Panacea.docx |
| LAST MODIFICATION DATE | 12.2.2019 |
| FILE FORMAT | docx |
| NUMBER OF TABLES | 25 |

(ii)

| TABLE OBJECT | |
|---|---|
| ATTRIBUTE | DESCRIPTION |
| PARENT DOCUMENT | <<LINK TO PARENT DOCUMENT OBJECT>> |
| PARENT FILE NAME | Panacea.docx |
| PARENT FILE PATH | Submissions/cureforall/Panacea.docx |
| INDEX IN DOCUMENT | 16 |
| TABLE TYPE | CSR |
| TITLE | Table 10. Demographic Characteristics |
| TABLE NUMBER | 10 |
| TABLE FOOTNOTES | Source: Table 14.1.2 Body mass index was calculated as weight/(height*0.01)$^2$ SD = STANDARD DEVIATION |
| NUMBER OF COLUMNS | 4 |
| NUMBER OF ROWS | 25 |
| SOURCE TABLE NUMBER | 14.1.2 |

(iii)

| TABLE CELL OBJECT | |
|---|---|
| ATTRIBUTE | DESCRIPTION |
| PARENT TABLE | <<LINK TO PARENT TABLE OBJECT>> |
| ROW INDEX | 3 |
| COLUMN INDEX | 2 |
| CELL VALUE | 7 |

INCIDENCE OF LABORATORY TEST ABNORMALITIES

| PARAMETER | CRITERIA | 25mg PANACEA CR | | | | | | 20mg PANACEA | |
|---|---|---|---|---|---|---|---|---|---|
| | | LOW-FAT | | MEDIUM-FAT | | HIGH-FAT | | MEDIUM-FAT EVENING MEAL | |
| | | N | n | N | n | N | n | N | n |
| HEMATOLOGY | | | | | | | | | |
| LYMPHOCYTES (%) | >1.2xULN | 7 | 8 | 2 | 2 | 3 | 1 | 10 | 2 |
| NEUTROPHILS (%) | <0.8xULN | 9 | 10 | 2 | 2 | 4 | 4 | 3 | 1 |
| BASOPHILS (ABS) | >1.2xULN | 6 | 9 | 9 | 3 | 8 | 2 | 7 | 2 |
| EOSINOPHILS (ABS) | >1.2xULN | 8 | 10 | 9 | 3 | 8 | 3 | 8 | 3 |
| EOSINOPHILS (%) | >1.2xULN | 11 | 3 | 3 | 2 | 8 | 2 | 4 | 5 |
| URINALYSIS (DIPSTICK) | | | | | | | | | |
| URINE NITRITE | >1 | 8 | 4 | 9 | 8 | 6 | 2 | 7 | 3 |

*F*

| TABLE CELL OBJECT | |
|---|---|
| ATTRIBUTE | DESCRIPTION |
| PARENT DOCUMENT | <<LINK TO PARENT TABLE>> |
| PARENT INDEX | 4 |
| COLUMN INDEX | 1 |
| CELL VALUE | >2.2xULN |
| SOURCE CELLS | <<EMPTY PLACEHOLDER>> |
| ROW HEADERS | PARAMETER; HEMATOLOGY; LYMPHOCYTES(%) |
| COLUMN HEADER | CRITERIA |
| ROW OR COLUMN HEADER FLAG | ROW HEADER |
| HEADER SCOPE | <<LINK TO AFFECTED HEADER CELL OBJECTS>> |

FIG. 6

|  | DRUG A | DRUG B | TOTAL (N=23) |
|---|---|---|---|
|  | n (%) | n (%) | n (%) |
| COMPLETE RESPONSE | 10 (72.7) | 4 (33.5) | IN TEXT VALUE: 33.(33.0)<br>SOURCE VALUE: 31.(31.0)<br>MORE DETAILS<br>DISMISS  ADD TO FIXES |
| PARTIAL RESPONSE | 5 (12.7) | 2 (14.2) |  |
| STABLE DISEASE | 9 (24.5) | 3 (12.3) |  |
| OBJECTIVE PROGRESSION | 8 (22.6) | 4 (32) |  |
| INDETERMINATE | 15 (13.8) | 2 (13) | 4 (13.3) |
| OBJECTIVE RESPONSE RATE | 15 (55.2) | 5 (60) | 12 (43.4) |
| 95% CI | (25.0, 58.4) | (12.3, 15.2) | (32.7, 53.2) |

FIG. 7

SYSTEM AND METHOD FOR VALIDATING TABULAR SUMMARY REPORTS

CROSS-REFERENCE TO RELATED APPLICATIONS

This application is a National Phase filing of International Application No. PCT/IL2020/050421 filed Apr. 7, 2020 which claims priority from U.S. Provisional Patent Application No. 62/831,766 filed Apr. 10, 2019 which is hereby incorporated in its entirety by reference.

FIELD OF THE INVENTION

The present invention relates to clinical study reports generally and to data validation in particular.

BACKGROUND OF THE INVENTION

Clinical trials carried out by pharmaceutical companies produce copious amounts of data which is typically analyzed by appropriate standard statistical packages such as SAS software (commercially available from SAS Institute Inc.). These packages analyze the data and summarize it into tables. The summarized tables (known as source documents or files) are then exportable in various formats.

A medical writer uses the source documents to manually produce clinical study reports (CSRs). A Clinical Study Report (CSR) is a document that provides details about the methods and results of a trial and resembles a peer-reviewed scientific paper. Just like any scientific paper, it uses tables to summarize and present the results.

The pharmaceutical company, accountable for its data validity, invests considerable resources in validating the CSR data before its submission to the regulator. The finished CSR is typically manually validated against the corresponding source documents (often using hard copies of the tables from both documents) to look for inconsistencies in the CSR. The process requires going over each table in the CSR, assembling the referenced source files and then visually scanning through each table cell to verify that the data is correct by tracing it to its source table and comparing the values.

SUMMARY OF THE PRESENT INVENTION

There is provided in accordance with a preferred embodiment of the present invention, a system including a processor and a unit running on the processor, the unit to validate and correct clinical summary reports, the unit including a parser to parse a clinical summary report and at least one associated source report at document, table and cell level and to generate a table object for each table in each report together with a matrix of cells for each the table, each matrix cell represented as a table cell object having an index; an identifier to identify each individual table cell object, the table cell objects being a title, a column header object, a row header object, a footnote and a result object; a fingerprint generator to determine a semantic fingerprint for each cell object, including a value, header text and row and column information; a cell matcher to match clinical study report table cell objects with corresponding linked source report table cell objects using the fingerprint; and a validator to compare values between the matched clinical study report table cell objects and the at least one associated table cell source report objects to provide a validation decision.

Moreover, in accordance with a preferred embodiment of the present invention, the system also includes a linker to link table objects of the summary report with table objects of one of the at least one source report using the footnote objects.

Further, in accordance with a preferred embodiment of the present invention, the system also includes a database to store document, table and table cell objects from the output of the parser; and a database updater to update the document, the table and the table cell objects from the output of the identifier, the linker, the matcher and the validator.

Still further, in accordance with a preferred embodiment of the present invention, the identifier includes a header identifier to determine best fit patterns for header objects based on features and to identify the column header object and the row header object from the patterns; and a scope identifier to identify the hierarchical structure with respect to other headers of the column header object and the row header object.

Additionally, in accordance with a preferred embodiment of the present invention, the validator includes a report creator to create a report from the output of the validator, the report creator to flag error table cell objects and to present a corrected value for the error table cell objects from the matched table cell objects of the associated source table.

Moreover, in accordance with a preferred embodiment of the present invention, the flag is a pop-up interface.

Further, in accordance with a preferred embodiment of the present invention, the linker creates an alert for missing sources.

Still further, in accordance with a preferred embodiment of the present invention the table object stores the file name of the corresponding document, an index, a type, a title, an identifying number, footnote information, number of columns, number of rows and a reference to source table numbers.

Additionally, in accordance with a preferred embodiment of the present invention, the table cell object stores a link to its parent table, a row and column index, a header scope and a value.

Moreover, in accordance with a preferred embodiment of the present invention, the parser parses according to predefined rules for different formats of documents.

There is provided in accordance with a preferred embodiment of the present invention, a method for validating and correcting clinical summary reports, the method includes parsing a clinical summary report and at least one associated source report at document, table and cell level; generating a table object for each table in each report together with a matrix of cells for each table, each matrix cell represented as a table cell object having an index; identifying each individual table cell object, the table cell objects being a title, a column header object, a row header object, a footnote and a result object; determining a semantic fingerprint for each cell object, including a value, header text and row and column information; matching clinical study report table cell objects with corresponding linked source report table cell objects using the fingerprint; and comparing values between the matched clinical study report table cell objects and the at least one associated table cell source report objects to provide a validation decision.

Moreover, in accordance with a preferred embodiment of the present invention, the method also includes linking table objects of the summary report with table objects of one of the at least one source report using the footnote objects.

Further, in accordance with a preferred embodiment of the present invention, the method includes storing document, table and table cell objects from the output of the parsing; and updating the document, the table and the table cell objects from the output of the identifying, the linking, the matching and the validating.

Still further, in accordance with a preferred embodiment of the present invention, the identifying includes determining best fit patterns for header objects based on features and identifying the column header object and the row header object from the patterns; and identifying the hierarchical structure with respect to other headers of the column header object and the row header object.

Additionally, in accordance with a preferred embodiment of the present invention, the validating includes creating a report from the output of the validating, the creating a report to also flag error table cell objects and to present a corrected value for the error table cell objects from the matched table cell objects of the associated source table.

Additionally, in accordance with a preferred embodiment of the present invention, the flag is a pop-up interface.

Moreover, in accordance with a preferred embodiment of the present invention, the linking creates an alert for missing sources.

Further, in accordance with a preferred embodiment of the present invention, the table object stores the file name of the corresponding document, an index, a type, a title, an identifying number, footnote information, number of columns, number of rows and a reference to source table numbers.

Still further, in accordance with a preferred embodiment of the present invention, the table cell object stores a link to its parent table, a row and column index, a header scope and a value.

Additionally, in accordance with a preferred embodiment of the present invention, the parsing is according to predefined rules for different formats of documents.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 1A and 1B are schematic illustrations of an example clinical study report (CSR) document and an example source document;

FIG. 4 is a schematic illustration of the database representation of document, table and table cell objects, constructed and operative in accordance with the present invention;

FIG. 6 is a schematic illustration of typical CSR table and the database representation of a single table cell within the table, constructed and operative in accordance with the present invention; and FIG. 7 is a schematic illustration of an example error report, constructed and operative in accordance with the present invention.

Figure 2:
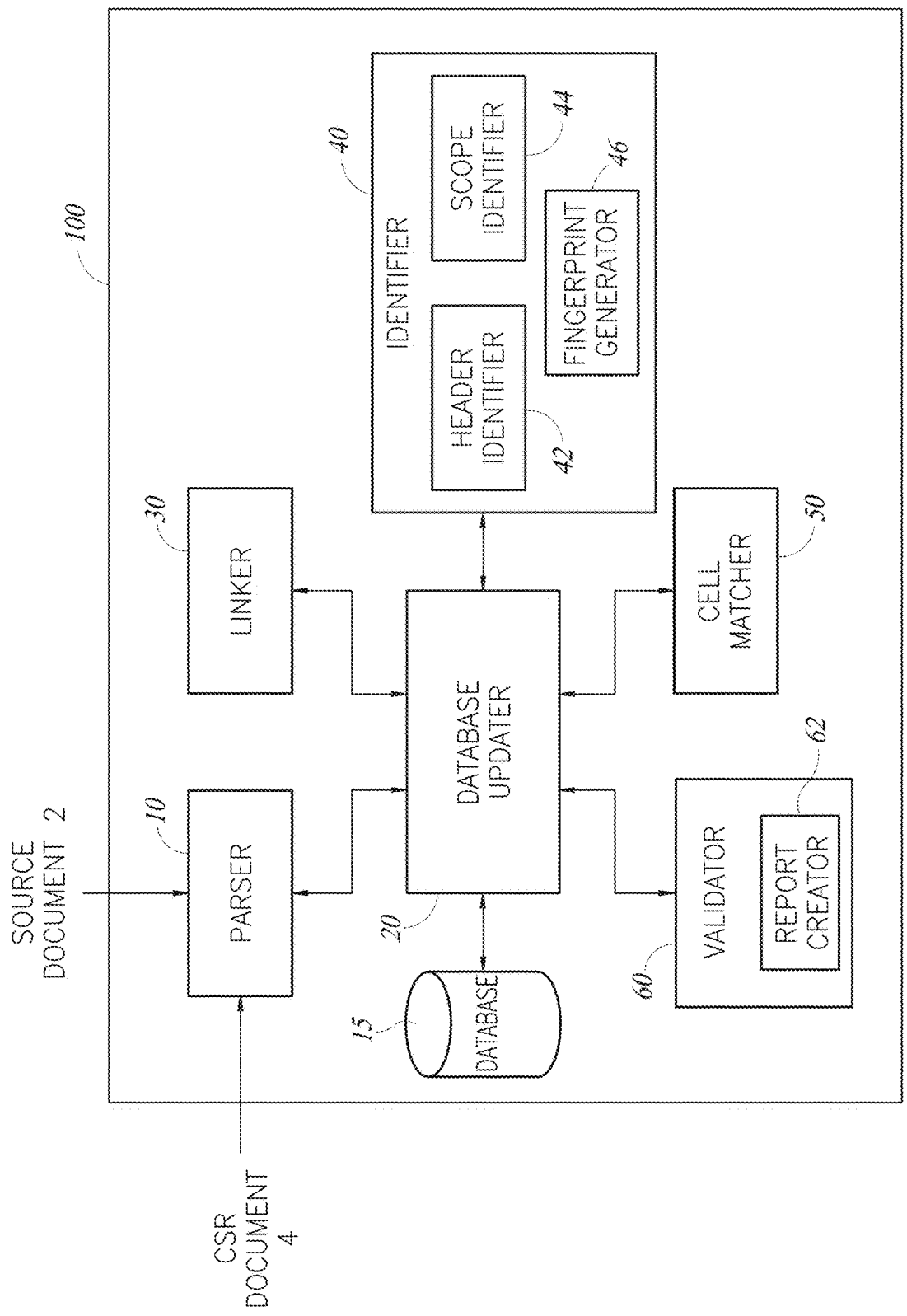
FIG. 2 is a schematic illustration of a system for validating clinical summary reports, constructed and operative in accordance with the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicants have realized that the manual validation of clinical study reports (CSRs) may be laborious and time consuming and may still have an error margin between the results shown in a finished CSR and its corresponding source documents.

Often the medical writers may combine data from more than one source table into a single CSR table or may change the format of the original table such as merging table cells, changing the order of readings, adding extra sub headers etc. making it difficult to visually matchup readings from both tables.

Reference is now made to FIG. 1A which illustrates a typical CSR document 10 (as discussed herein above) and FIG. 1B which illustrates a typical source document 10A. For both type of document, each table may have table cells associated with rows and columns, with headers and sub headers. As is illustrated, CSR document 10 may contain a text description A added by the medical writer, at least one table B and more text in the form of footnotes C. Footnote C may include a reference to the source tables used to create the document (in this scenario 14.1.2.3.4.). Source document 10A may contain multiple tables such as table D. For all tables, each table cell may be part of a header or a result value.

Applicants have realized that each cell in a table not only holds a value, but also has a "fingerprint" i.e. a meaning or representation for the table cell providing semantic information about the table cell and therefore making it unique. This information may be used to identify a particular table cell based on positioning, headers, text and row/column information providing context as well as type (header, result value etc.) for each table cell.

Applicants have further realized that a more efficient method of validating CSRs is by using a method of automated computer validation based on this semantic fingerprint. The CSR and source documents containing the pertinent corresponding tabular data are parsed and represented in a database. Documents, tables, and cells are analyzed to provide exhaustive information for each document and links are added between source documents and CSR tables. Row and column headers are then identified including their hierarchical structure and scope of effect. At each stage in the process, database records are updated accordingly at the document, table and table cell levels with the final table cell object at the end of the process providing the "fingerprint".

CSR table cells are then matched with their corresponding source table cells using these "fingerprints", and finally the values are validated. Machine learning and natural language processing techniques are used to carry out the analyses and matching. The system flags errors it automatically identifies and suggests possible corrections.

Reference is now made to FIG. 2 which illustrates a unit or system 100 for validating clinical summary reports in accordance with an embodiment of the present invention. System 100 may comprise a parser 10, a database 15, a database updater 20, a linker 30, an identifier 40, a cell matcher 50 and a validator 60. Identifier 40 may further comprise a header identifier 42 a scope identifier 44 and a fingerprint generator 46. Validator 60 may further comprise a report creator 62. The functionality of the elements is discussed in more detail herein below.

It will be appreciated that system 100 may be implemented for any sets and types of documents having a summary report with tables and a corresponding source document. For the sake of illustration, the discussion below will use the example of a CSR document as described herein above.

Figure 3:
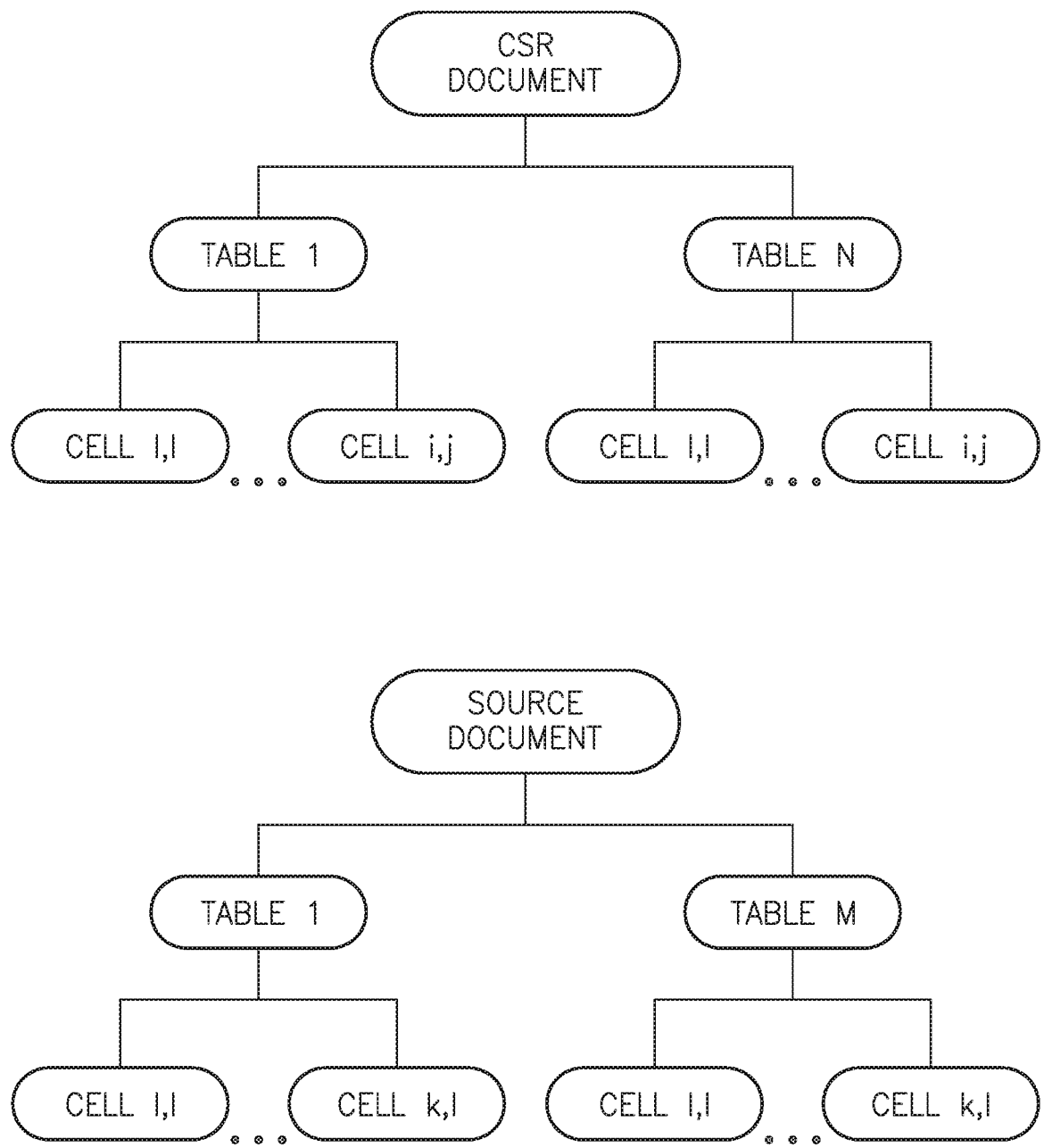
FIG. 3 is a schematic illustration of how CSR documents and source documents are broken down to table and table cell level, constructed and operative in accordance with the present invention.

Parser 10 may receive the CSR document (4) and all relevant source documents (2) and may parse these files to extract data at the document, table and cell levels. Reference is now made to FIG. 3 which illustrates how both document types may be parsed and represented in the database as document, table and cell objects for a CSR document comprising N tables and a source document comprising M tables. Each CSR table may have i rows and j columns and each source table may have k rows and l columns. It will be appreciated that the values of i, j and k, l may vary from table to table. The extracted information may be stored in database 15 by database updater 20. It will be appreciated that parser 10 may use rule-based algorithms in order to read each document and extract relevant information. It will be further appreciated that although CSR documents may typically be in Word or pdf format, source documents may come in many different formats such as txt, rpt, doc, html, pdf etc. Parser 10 may automatically determine the format of each input file and apply an appropriate parsing scheme accordingly.

It will be appreciated that according to the format of the document to be parsed, parser 10 may utilize pre-defined rules. It will be further appreciated that since the rules are format associated, parser 10 may know to look for specific features depending on the file format such as dashes, indentations, coherence between cells etc. to identify sections of documents. For example, parser 10 may know that for a particular format, a dashed line may represent part of a table border. Thus, for each file format, parser 10 may recognize titles, footnotes, tables, table cells etc.

It will also be appreciated that parser 10 may parse the tables recursively to find the lowest coherent level and may only identify data at document, table and table cell level. Parser 10 may not identify headers, result values etc. which are not indicated in the table formats, these may be identified by the elements of identifier 40 as described in more detail herein below. It will also be appreciated that parser 10 may create a matrix holding the data or content of each parsed table, thus each matrix cell (and therefore each table cell object) may have a cell column and row index i.e. each matrix cell may have a "coordinate" within the matrix and a value as is shown in FIG. 3.

It will also be appreciated that during the parsing process, parser 10 may also identify special symbols which may be format specific (such as Microsoft representations) and may convert them to a universal format.

As discussed herein above, database updater 20 may update database 15 accordingly. It will be appreciated that database 15 may hold inter-related objects for documents, tables and table cells accordingly. Reference is now made to FIG. 4 which illustrates typical records for document, table and table cell objects with each object having its own unique list of attributes.

As is shown in FIG. 4 and discussed herein above, the parsed document, table and table cell objects may have information stored for each level. For example, as shown in example i for a document object, its corresponding record may hold information regarding its filename, file path, its file format, its last modification date, the number of tables it holds. A record for a table object (example ii) may hold information such as its corresponding parent document and file name, an index, a type, a title, an identifying number, footnote information, number of columns, number of rows and a reference to source table numbers. A record for a table cell object (example iii) may hold (at this stage), a link to its parent table, its row and column index (from the resulting matrix as discussed herein above) and finally the value of the table cell.

Figure 5:
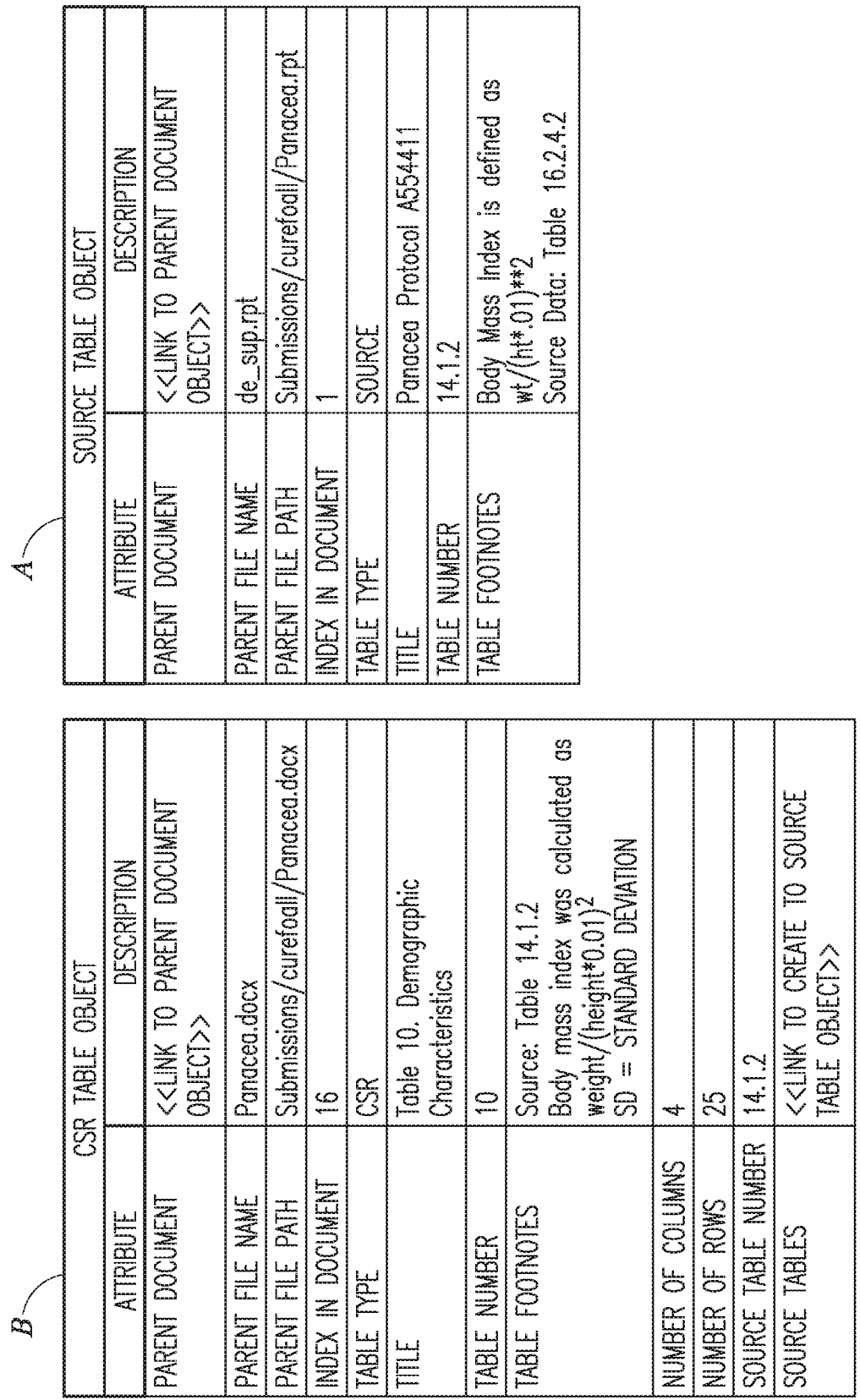
FIG. 5 is a schematic illustration of the database representation of a CSR table object linked to a corresponding source table object, constructed and operative in accordance with the present invention.

Linker 30 may link CSR table objects with their corresponding source table objects as is illustrated in FIG. 5 to which reference is made at the database level. Linker 30 may utilize a suitable database query which may match the table number of the table object in the source document, with the extracted table number from the footnote attribute of the CSR table. Database updater 20, may update the table object records with this information accordingly. For example, as is shown in FIG. 5 to which reference is now made, table number 14.1.2 in the source table object A, matches the table number appearing in the table footnotes of the CSR table object B. Linker 30 may also create an alert for missing sources.

As discussed herein above, each table cell object parsed from the tables may have a row and column index and content (as discussed herein above in relation to the matrix), but no indication of whether the cell belongs to the header of a table or to its body (i.e. holds a result value). Identifier 40 may utilize machine learning and natural language processing techniques in order to determine the type of table cell object i.e. column header object, a row header object, or a result object and the relationships between them. i.e. if the object is a result, identifier 40 may determine which headers it belongs to. If the object is a header, it may also determine what its scope of effect is and its hierarchical structure in respect with other headers (header, sub-header). As discussed herein above, identifier 40 may comprise a header identifier 42 and a scope identifier 44.

It will be appreciated that header identifier 42 may receive from database 15 a row or column of cells in a table as input and the output for each may be a probability of the column or the row of cells being a row header or a column header of a table. It will also be appreciated that system 100 may recognize rows or columns of cells from the results of parser 10.

Header identifier 42 may use the information stored for the table cell objects in database 15 together with machine learning techniques to determine the best fit pattern for header objects based on features. For example, header identifier 42 may know the number of rows and columns in the pertinent table to which the objects belong, the number of repeated elements in a column or row (such as 'n, %, n, %, n, %' vs '4, 12, 4, 6, 7, 2'; cells separated by commas).

Header identifier 42 may also know the alpha ratio (the average ratio of alphabetic characters in a column or row), the capitalization ratio (the average ratio of upper-case alphabetic characters in a column or row), the average number of spaces in a column or row, the average number of tokens within column or row objects, etc.

Header identifier 42 may also use a classifier or decision tree and may continually "learn" patterns by receiving multiple examples of different patterns where it is known whether a column or a row is a header or not. On this basis, it may extract appropriate patterns for unseen input without known attribution to header or non-header class.

Reference is now made to FIG. 6 which illustrates a typical CSR table G and the object representation F of a single table cell belonging to table G. As can be seen, headers may be hierarchical or nested (i.e. 25 mg panacea may be further divided into sub-headers of low-fat, medium-fat and high fat and each sub-header may further be divided into n and %). Headers may also have a scope, i.e. the result objects that belong to it. Like header identifier 42, scope identifier 44 may also utilize machine learning and natural language techniques to determine the scope of a header column or row. Thus, for each identified header table cell object (column or row header), scope identifier 44 may determine the scope by the effect it has on its pertinent table cells i.e. which other objects are also affected by the header. Therefore, scope identifier 44 may determine for each table cell object, which headers it belongs to and their corresponding hierarchy.

Features taken into account by scope identifier 44 may include but not be limited to an empty neighboring table cell (an indication whether a table cell below or to the right is empty), an indentation before a table cell value (i.e. the number of spaces before a value in a table cell e.g. ' number of subjects' vs. 'number of subjects') and a header neighbor table cell (an indication whether the table cell below or to the right is a header cell). Other features may include the numeric ratio difference (the difference between header cell numeric character ratio and the tested cell ratio), capitalization ratio (the difference between the header cell upper case character ratio and the tested cell ratio) and the number of token difference (the difference between header cell number of tokens and the tested cell).

Scope identifier 44 may also use a classifier or decision tree and may continually "learn" by receiving multiple examples of different patterns where it is known where a header and its scope lies. On this basis, it may extract appropriate patterns for new input.

As is shown in FIG. 6 back to which reference is now made, the table cell object record F now holds information regarding row headers, column headers, row/column tags and header scope. Therefore fingerprint generator 46 may use this information to generate a semantic fingerprint for each table cell object providing semantic information about the table cell and therefore making it unique as discussed herein above.

It will be appreciated that database updater 20 may update the table cell records in database 20 accordingly using the output from both header identifier 42, scope identifier 44 and fingerprint generator 46.

As discussed herein above, CSR tables may be made up of more than one source table or a partial source table. Medical writers when creating their reports, may also change the view of a table (i.e. change headers, change the order of cells, integrate multiple source tables, etc.) As a result, a direct source table cell/CSR table cell based on linked table match may be irrelevant. Moreover, a single CSR table cell may display multiple values that originate from multiple source table cells.

It will be appreciated that once the table cells have been classified accordingly (as discussed herein above), this information may be used to match a CSR table cell object with its source cell object (as can be seen in FIG. 6, at this stage the source cells matching cell list attribute is empty in table cell object F). As discussed herein above CSR tables are linked to their source tables via linker 30.

Cell matcher 50 may also use machine learning and natural language processing techniques to determine whether a table cell object from a CSR document can be correctly matched with a table cell object from a source document by comparing their fingerprints based on semantic matching. Cell matcher 50 may learn from examples of known CSR table cells and their known corresponding matching source table cells in order to learn patterns to generalize and make predictions for new unseen examples. It will be appreciated that the output of cell matcher 50 is the probability that the source table cell object is the source for a CSR table cell object and that cell matcher 50 may determine if there is a match based on comparison of the probability with pre-defined threshold values.

It will also be appreciated that cell matcher 50 may take into account various features when attempting to find a match. These features may include header similarity (information extracted by header identifier 30 and scope identifier 40) both structurally and semantically. For example, the text in a header "number of subjects" and "n participants" are close semantically but far apart structurally or syntactically. Other features may include but not be limited to the number of matching tokens in a header (e.g. the count of the tokens that match between CSR table cell headers and source table cell headers), a dosage match (e.g. if there is a dosage mentioned in the header, an indication of whether the dosages match) and a parameter match (e.g. if there is a parameter mentioned in a header such as "mean" and "std").

Cell matcher 50 may compare the meaning of clauses from headers, or entire headers by using state of the art natural language processing algorithms such as word embedding. Word embedding is known in the art as a learned representation for text where words that have the same meaning have a similar representation as described in the article "Distributed Representation of Words and Phrases and their Compositionality" by Mikolov et al. published 2013 in Neural Information Processing Systems pages 3111-3119. Thus, the word embedding vector space may represent words and phrases in a manner that retains their semantic meaning. Cell matcher 50 may assign a numerical vector to each occurrence of a word or phrase and may apply simple mathematical operations to the vectors to test their semantic distance or relationships.

Once the correct table cells have been matched, database updater 20 may update the table cell objects accordingly to indicate the match.

Finally, cell validator 60 may validate whether the value in the CSR table cell corresponds with the value in its associated source table cell (or cells). Cell validator 60 may use a rule-based algorithm to compare the two cells. It will be appreciated that since CSR table cells may often have more than a single value (e.g. number of subject and % of total) or multiple matching cells and values within source cells, cell validator 60 may compare sets of values and provide a validation decision for the case. As discussed herein above, cell validator may use rule-based algorithms to analyze the two sets of values (the CSR table cell and corresponding source table cell or cells) and compare them.

The output may be a binary indication of whether the table cell is validated or whether there is a suspected error.

Report creator 62 may create a summary report for each CSR table, based on the results of cell validator 60. with any suspect table cell objects or pop up accordingly in a user interface, based on the binary output and present it to the user as is illustrated in FIG. 7 to which reference is now made. FIG. 7 represents an example summary report table X showing shaded cells Y where there is an error flagged by system 100. As can be seen, the value 33 was added to the CSR by the medical writer instead of the correct source value 31 as parsed from the source document. When the pertinent table cell is selected, a pop-up interface Z may provide further details. The summary report may also present a corrected value to the user. This corrected value may be the source table cell value i.e. the original value.

Thus, both CSRs and their associated source documents may be parsed and analyzed in order to determine and identify value table cells together with a unique semantic fingerprint in order to accurately match the values between the CSR tables and their associated source documents. Once table cells are matched, the values may be compared in order to automatically validate clinical summary reports.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type, such as a client/server system, mobile computing devices, smart appliances, cloud computing units or similar electronic computing devices that manipulate and/or transform data within the computing system's registers and/or memories into other data within the computing system's memories, registers or other such information storage, transmission or display devices.

Embodiments of the present invention may include apparatus for performing the operations herein. This apparatus may be specially constructed for the desired purposes, or it may comprise a computing device or system typically having at least one processor and at least one memory, selectively activated or reconfigured by a computer program stored in the computer. The resultant apparatus when instructed by software may turn the general purpose computer into inventive elements as discussed herein. The instructions may define the inventive device in operation with the computer platform for which it is desired. Such a computer program may be stored in a computer readable storage medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus. The computer readable storage medium may also be implemented in cloud storage.

Some general purpose computers may comprise at least one communication element to enable communication with a data network and/or a mobile communications network.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A system comprising:
    a processor; and
    a unit running on said processor, said unit to validate and correct clinical summary reports, said unit comprising:
        a parser to parse a clinical summary report and at least one associated source report at document, table and cell level and to generate a table object for each table in each said report together with a matrix of cells for each said table, each matrix cell represented as a table cell object having an index;
        an identifier to identify each individual table cell object, said table cell objects being a title, a column header object, a row header object, a footnote and a result object;
        a fingerprint generator to determine a semantic fingerprint for each cell object, comprising a value, header text and row and column information;
        a cell matcher to match clinical study report table cell objects with corresponding linked source report table cell objects using said semantic fingerprint;
        a validator to compare values between said matched clinical study report table cell objects and at least one associated table cell source report object to provide a validation decision; and
        a linker to link table objects of said clinical summary report with table objects of one of at least one source report using footnote objects.

2. The system according to claim 1 and also comprising:
    a database to store document, table and table cell objects from the output of said parser; and
    a database updater to update said document, said table and said table cell objects from the output of said identifier, said linker, said cell matcher and said validator.

3. The system according to claim 1 wherein said identifier comprises:
    a header identifier to determine best fit patterns for header objects based on features and to identify said column header object and said a row header object from said patterns; and
    a scope identifier to identify the hierarchical structure with respect to other headers of said column header object and said row header object.

4. The system according to claim 1 wherein said validator comprises a report creator to create a report from the output of said validator, said report creator to flag error table cell objects and to present a corrected value for said error table cell objects from the matched table cell objects of an associated source table.

5. The system according to claim 4 wherein said flag is a pop-up interface.

6. The system according to claim 1 wherein said linker creates an alert for missing sources.

7. The system according to claim 1 wherein a table object stores the file name of the corresponding document, an index, a type, a title, an identifying number, footnote information, number of columns, number of rows and a reference to source table numbers.

8. The system according to claim 1 wherein said table cell object stores a link to its parent table, a row and column index, a header scope and a value.

9. The system according to claim 1 wherein said parser parses according to pre-defined rules for different formats of documents.

10. A method for validating and correcting clinical summary reports, said method comprising:
   parsing a clinical summary report and at least one associated source report at document, table and cell level;
   generating a table object for each table in each said report together with a matrix of cells for each said table, each matrix cell represented as a table cell object having an index;
   identifying each individual table cell object, said table cell objects being a title, a column header object, a row header object, a footnote and a result object;
   determining a semantic fingerprint for each cell object, comprising a value, header text and row and column information;
   matching clinical study report table cell objects with corresponding linked source report table cell objects using said semantic fingerprint;
   comparing values between said matched clinical study report table cell objects and at least one associated table cell source report object to provide a validation decision; and
   linking table objects of said clinical summary report with table objects of one of at least one source report using footnote objects.

11. The method according to claim 10 and also comprising:
   storing document, table and table cell objects from the output of said parsing; and
   updating said document, said table and said table cell objects from the output of said identifying, said linking, said matching and said validating.

12. The method according to claim 10 wherein said identifying comprises:
   determining best fit patterns for header objects based on features and identifying said column header object and said row header object from said patterns; and
   identifying the hierarchical structure with respect to other headers of said column header object and said row header object.

13. The method according to claim 10 wherein said validating comprises creating a report from the output of said validating, said creating a report to also flag error table cell objects and to present a corrected value for said error table cell objects from the matched table cell objects of an associated source table.

14. The method according to claim 13 wherein said flag is a pop-up interface.

15. The method according to claim 10 wherein said linking creates an alert for missing sources.

16. The method according to claim 10 wherein a table object stores the file name of the corresponding document, an index, a type, a title, an identifying number, footnote information, number of columns, number of rows and a reference to source table numbers.

17. The method according to claim 10 wherein said table cell object stores a link to its parent table, a row and column index, a header scope and a value.

18. The method according to claim 10 wherein said parsing is according to pre-defined rules for different formats of documents.

* * * * *